United States Patent [19]

Terada et al.

[11] 4,134,793

[45] Jan. 16, 1979

[54] CREATININE DESIMIDASE IN THE QUANTITATIVE DETERMINATION OF CREATININE

[75] Inventors: Osamu Terada; Takayuki Uwajima, both of Machida, Japan

[73] Assignee: Kyowa Hakko Kogyo Co., Ltd., Tokyo, Japan

[21] Appl. No.: 842,979

[22] Filed: Oct. 17, 1977

Related U.S. Application Data

[62] Division of Ser. No. 711,207, Aug. 3, 1976, Pat. No. 4,087,329.

[30] Foreign Application Priority Data

Aug. 28, 1975 [JP] Japan .............................. 50-103473
Sep. 11, 1975 [JP] Japan .............................. 50-109452

[51] Int. Cl.² .......................................... G01N 31/14
[52] U.S. Cl. ........................................... 195/103.5 R
[58] Field of Search ................... 195/103.5 R, 62, 65, 195/66 R

[56] References Cited

U.S. PATENT DOCUMENTS

| 3,806,420 | 4/1974 | Holz et al. | .......................... 195/66 R |
| 4,039,384 | 8/1977 | Suzuki et al. | ...................... 195/65 X |

OTHER PUBLICATIONS

Szulmajster, Journal of Bacteriology vol. 75, 663 (1958).

*Primary Examiner*—Lionel M. Shapiro
*Attorney, Agent, or Firm*—Fitzpatrick, Cella, Harper & Scinto

[57] ABSTRACT

Creatinine desimidase is produced by fermentation of microorganisms belonging to the genera Brevibacterium, Corynebacterium, Pseudomonas and Arthrobacter. The enzyme is recovered from the microbial cells and culture liquor. The enzyme is used for the quantitative determination of creatinine in a sample.

7 Claims, No Drawings

CREATININE DESIMIDASE IN THE QUANTITATIVE DETERMINATION OF CREATININE

This is a division of application Ser. No. 711,207, filed Aug. 3, 1976 now U.S. Pat. No. 4087,329, issued May 2, 1976.

BACKGROUND OF THE INVENTION The present invention relates generally to creatinine desimidase, its method of production and the use thereof for the quantitative determination of creatinine.

Creatinine is a metabolic waste product formed by non-enzymatic dehydration of creatine which is produced from creatinephosphoric acid, one of the sources of muscular contractile energy. Creatinine is not utilized in vivo and is excreted as an end metabolite in urine. Creatinine also exists in blood in a normal concentration of about 0.7–1.5 mg/100 ml of serum. The determination of the amount of creatinine in blood and urine is, therefore, very useful for diagnostic purposes in the determination of kidney diseases such as acute nephritis and chronic nephritis and of disorders such as urethrophraxis, mercurialism, nephrosis, etc.

Heretofore, the quantitative determination of creatinine has been carried out according to colorimetric determination utilizing Jaffe's reaction which comprises a color reaction with alkaline picrate. While colorimetric determination of creatinine using alkaline picrate is practical in that the operation is simple and stable, this method involves certain defects. That is, because of poor sensitivity, the use of an increased amount of serum is necessary; the reaction is not specific; and the reaction is subject to the influence of substances in the blood such as an active methylene compound, proteins, antibiotics, etc. In order to overcome these defects, it is necessary to remove the substances in the sample or to extract the creatinine. However, such operations complicate the procedure and, therefore, are disadvantageous for automatic operation.

It has now been found that the amount of creatinine in a sample can be determined more simply, more correctly and more speedily as compared to the heretofore known method, by decomposing creatinine using an enzyme which catalyzes a reaction wherein creatinine is hydrolyzed into N-methyl-hydantoin an ammonia and then measuring the amount of the formed N-methyl-hydantoin or ammonia.

The catalytic enzyme employed in the process of the present invention is creatinine desimidase.

Creatinine desimidase (EC 3.5.4.21) was reported by J. Szulmajster (J. Bacteriology 75, 633, 1958 and Biochimica Et Biophysica Acta 30, 1954, 1958) in the microbial cells of *Clostridium paraputrificum* in 1958. The enzyme participates in the decomposition of creatinine and catalyzes a reaction to hydrolyze creatinine to form N-methyl-hydantoin and ammonia.

However, microorganisms of the genus *Clostridium* are anaerobic and when they are used for the production of the enzyme, a long period of time is required for the fermentation, microbial growth is poor and the yield of the enzyme is poor. Therefore, it has not been possible to carry out the production of creatinine desimidase on an industrial scale.

Other prior investigators have reported findings of strains of aerobic organisms belonging to the genus *Pseudomonas* which could decompose creatinine. However, none of these prior investigators have reported a microorganism which produces an enzyme capable of catalyzing an hydrolysis reaction wherein creatinine is decomposed to form N-methyl-hydantoin and ammonia. Moreover, such prior investigators were unable, according to the published reports, to isolate a particular enzyme capable of catalyzing the above-mentioned reaction.

It has now been found that microorganisms of the genera Brevibacterium, Corynebacterium, Pseudomonas and Arthrobacter, when cultured in a nutrient medium, produce remarkable amounts of creatinine desimidase in the culture liquor and/or within the microbial cells.

The creatinine desimidase obtained according to the present invention may be readily used for the quantitative determination of the amount of creatinine in a sample in an automatic operation not heretofore attainable. More specifically, the amount of creatinine in a sample can be simply and quickly determined by measuring the amount of N-methyl-hydantoin or ammonia formed through the catalytic action of the enzyme.

SUMMARY OF THE INVENTION

In accordance with the present invention, creatinine desimidase is produced by culturing a microorganism belonging to the genus Brevibacterium, Corynebacterium, Pseudomonas or Arthrobacter and capable of producing creatinine desimidase in a nutrient culture medium, until creatinine desimidase is formed in the culture liquor and/or within the microbial cells and thereafter recovering the creatinine desimidase.

The amount of creatinine is determined by reacting the creatinine desimidase thus produced with a sample containing creatinine to catalyze the reaction to hydrolyze creatinine into N-methyl-hydantoin and ammonia, measuring the amount of at least one of the N-methyl-hydantoin and ammonia produced and thereafter calculating the amount of creatinine in the sample.

DESCRIPTION OF THE INVENTION

In accordance with the present invention, when a microorganism belonging to the genus Brevibacterium, Corynebacterium, Pseudomonas or Arthrobacter and having an ability to produce creatinine desimidase is cultured in a nutrient medium containing an appropriate carbon source, nitrogen source, inorganic materials and other nutrients, creatinine desimidase is formed in the culture liquor and/or within the microbial cells, which is thereafter recovered.

In the present invention, any microorganism that belongs to the genus Brevibacterium, Corynebacterium, Pseudomonas or Arthrobacter which has the ability to produce creatinine desimidase may be used. Examples of the presently preferred strains are as follows:

(1) *Brevibacterium ammoniagenes* KY 3462
(2) *Brevibacterium divaricatum* KY 3810
(3) *Corynebacterium lilium* KY 3509
(4) *Corynebacterium glutamicum* KY 3801
(5) *Pseudomonas ovalis* KY 4651
(6) *Pseudomonas cruciviae* KY 3961
(7) *Arthrobacter ureafaciens* KY 3152
(8) *Arthrobacter histidinolovorans* KY 3158

The microbiological properties of the species of the above (1), (6) and (7) are described in Bergey's manual of Determinative Bacteriology, 7th Ed., pages 499, 114 and 610, respectively. The microbiological properties of the species of the above (2) are described in Japanese Pat. Publication No. 20294/63 and those of the species of (3) are described in U.S. Pat. No. 3,087,863. Further, the microbiological properties of the species of (4) are described in J. Gen. Appl. Microbiol., 13,279-301, 1967, those of the species of (5) in Bergey's Manual of Determinative Bacteriology, 8th Ed., page 222 and those of the species of (8) in J. Biol. Chem. 209, 829 (1954).

The above-noted strains have been deposited with the Fermentation Research Institute, Agency of Industrial Science and Technology, Tokyo, Japan under FERM-P Nos. 3207, 3208, 3209, 3210, 3211, 3212, 3213 and 3214, respectively.

These strains have also been deposited with the American Type Culture Collection, Rockville, Md., U.S.A., and have been accorded accession numbers ATCC 31169, ATCC 14020, ATCC 15990, ATCC 31170, ATCC 31171, ATCC 31172, ATCC 7562 and ATCC 11442, respectively.

Either a synthetic or natural medium may be used for culturing of the microorganisms in the present invention so long as it contains a carbon source, a nitrogen source, inorganic materials and other nutrients which are assimilable by the particular strain utilized.

As the carbon source, various carbohydrates such as glucose, fructose, sucrose, maltose, mannose, starch, starch hydrolyzate liquor, molasses, etc., various sugar alcohols such as glycerol, sorbitol, mannitol, etc., organic acids such as acetic acid, lactic acid, pyruvic acid, fumaric acid, citric acid, etc., alcohols such as methanol, ethanol, etc., glycols such as ethylene glycol, propylene glycol, etc., amino acids and hydrocarbons such as n-hexadecane may be used.

As the nitrogen source, ammonia, inorganic and organic ammonium salts such as ammonium chloride, ammonium carbonate, ammonium phosphate, ammonium nitrate, ammonium acetate, etc., urea, amino acids and other nitrogen-containing compounds as well as nitrogenous organic materials such as peptone, NZ-amine, meat extract, corn steep liquor, casein hydrolyzate, chrysalis hydrolyzate, fish meal, its digested product, defatted soybean, its digested product, etc. may be used.

As the inorganic materials, potassium dihydrogenphosphate, dipotassium hydrogenphosphate, potassium chloride, magnesium sulfate, manganese sulfate, ferrous sulfate, sodium chloride, calcium carbonate, etc. are appropriate.

It has been found that the creatinine desimidase is an adaptive enzyme. Accordingly, in the process of the present invention, the yield of creatinine desimidase can be greatly enhanced by adding creatinine or a creatinine-containing natural substance such as fish meat extract and beef extract to the medium as an enzyme inducer.

Particularly good results are obtained by adding creatinine in an amount of 0.05 to 2% (W/V) to the medium.

Generally, culturing is carried out at a temperature of 15°-40° C., preferably, 28°-33° C. During culturing, the pH is maintained at 6.0-8.5, preferably, at 6.5-8.5. Culturing is continued until the enzyme is formed and detected in the culture liquor, generally for 20-30 hours. Under these conditions, a considerable amount of creatinine desimidase is formed in the culture liquor and/or within the microbial cells.

To recover the enzyme, the microbial cells are disrupted by any of the conventional methods such as ultrasonic disintegration, grinding, mechanical pressure, autolysis, etc. to obtain a cell extract. Extraction of creatinine desimidase from the culture liquor and from the cell extract is carried out in the following manner. First, a precipitate is obtained by using salts such as ammonium sulfate, sodium sulfate, etc. or solvents such as acetone, methanol, ethanol, etc. Where ammonium sulfate is used, the portion which dissolves in ammonium sulfate of 40% saturation and which precipitates in that of 70% saturation is recovered. Where acetone is used, the portion which precipitates in acetone of 60% concentration is recovered.

The precipitate obtained in this manner is then subjected to dialysis or gel filtration to remove the salt or solvent contained in the precipitate. For dialysis, a dialytic membrane such as, cellophane, bladder membrane, collodion membrane, etc. or appropriate. The preferred dialytic solvent is 0.01M phosphate buffer (pH 7.0). For gel filtration, the use of Sephadex G-25 or G-50 together with 0.01M phosphate buffer (pH 7.0) is preferred.

In order to remove nucleic acid from the membrane, an aqueous solution of protamine (containing an amount of protamine corresponding to one tenth of the protein content of the liquid within the membrane) is added dropwise with stirring and the resultant mixture is allowed to stand 0°-4° C. for about 30 minutes to form a precipitate. The formed precipitate is removed by centrifugation (10,000 × g, 20 minutes) and the supernatant is recovered.

The supernatant is then passed through a column of DEAE-cellulose previously treated with 0.01M phosphate buffer (pH 7.0). Thereafter, 0.01M phosphate buffer is passed through the column to elute impure protein. Then, elution is carried out according to the gradient elution method beginning with 0.01M phosphate buffer (pH 7.0) and ending with 0.1M phosphate buffer containing 0.3M NaCl (pH 7.0). The eluate is recovered in fractions. The activity of creatinine desimidase contained in each of the fractions is measured by the method described below and the active fractions are combined, to which two volumes of acetone is added to form a precipitate. The precipitate is collected by centrifugation and is subjected to dialysis. The liquid within the membrane is then freeze-dried to obtain purified creatinine desimidase in powdered form.

The enzymatic activity of creatinine desimidase is calculated by determining the amount of ammonia formed when creatinine is used as the substrate according to the indophenol method. More specifically, 0.5 ml of 1% aqueous creatinine hydrochloride solution, 0.5 ml of 0.1M phosphate buffer (pH 7.5), 0.4 ml of water and 0.1 ml of an enzyme solution are mixed and incubated at 37° C. for 10 minutes. To the mixture is added 1 ml of phenol solution (prepared by dissolving 5.0 g of phenol and 25 mg of sodium nitroprusside in enough water to make a volume of 500 ml) and the resulting mixture is stirred. To this mixture 1 ml of alkaline sodium hypochlorite solution [prepared by dissolving 2.5 g of sodium hydroxide in about 300 ml of water, adding 1.25 ml of sodium hypochlorite (containing 10% effective chlorine) thereto and then diluting the mixture with water to make a volume of 500 ml] is added and the mixture is stirred and allowed to stand at room temperature for 20 minutes. The absorbency at 630 m$\mu$ is measured by means of a photoelectric colorimeter. For control, the same operation is carried out using an enzyme solution previously heated at 100° C. for 5 minutes. The absorbency at 630 m$\mu$ of the control solution is subtracted from that at 630 m$\mu$ of the test solution.

Separately, the calibration curve of the concentration of ammonia and the absorbency at 630 mμ is obtained. From the value obtained by subtraction of absorbencies, the amount of the formed ammonia is obtained. Based on this, the enzymatic activity contained in the sample is calculated.

The enzymatic activity is indicated as a unit, one unit being defined as that amount of the enzyme which decomposes 1μ mole of creatinine at 37° C. and at pH 7.5 in one minute.

Creatinine desimidase obtained by the foregoing process of the invention acts characteristically upon creatinine and catalyzes the reaction to decompose creatinine into N-methyl-hydantoin and ammonia. The enzyme does not act upon creatine, creatinine phosphoric acid, urea, arginine, glutamic acid, canavanine, glutamine, cytosine, guanine, etc.

Determined by the gel-filtration method described in Biochemical Journal 96, 595, 1965 using Sephadex G-200, the molecular weight of creatinine desimidase is about 200,000.

The optimum pH of the enzyme when treated at 37° C. for 10 minutes is near 8 and the stable pH range when treated at 30° C. for 30 minutes is from 4.0 to 9.0. The optimum temperature of the enzyme in the reaction at pH 8.0 for 10 minutes is near 50° C. When treated at pH 7.0 for 30 minutes, the enzyme is stable up to 50° C. and loses about 20% of its activity at 55° C.

The action of the present enzyme is inhibited by 1 mM of heavy metal ions such as $Cu^{2+}$, $Hg^{2+}$, $Ag^+$, etc. and P-chloro-mercuri benzoic acid. Thus, it is believed that an SH group participates in the action of the enzyme.

Creatinine desimidase obtained in the above manner is particularly suitable for the other aspect of the present invention, i.e., the quantitative determination of the amount of creatinine in a sample. For example, this is readily accomplished by reacting a sample containing creatinine with a phosphate buffer solution containing an amount of 0.1 to 1.0 mg/ml of creatinine desimidase at a temperature of 30°–50° C. for about 10–30 minutes to hydrolyze the creatinine into N-methyl-hydantoin and ammonia, and then measuring the amount of the formed N-methyl-hydantoin or that of the formed ammonia.

The method of the present invention is applicable to the determination of the amount of creatinine in any sample containing creatinine and the method can preferably be applied particularly to the determination of the amount of creatinine in blood and urine. In carrying out the determination of the amount of creatinine in blood, a sample of blood is subjected to centrifugation at 2,500–3,000 r.p.m. for about 5 minutes and the serum obtained is used for the reaction. In the case of urine, the sample may be a specimen of urine as is or diluted to an appropriate concentration, generally two to five fold, with water.

The determination of the amount of N-methyl-hydantoin formed by the reaction can be carried out according to the method of Kirby and Berry described in Paper and Paperelectrophoresis, Academic Press, New York, page 348, 1958. Briefly described, the method comprises the addition of alkaline ferricyanide-nitroprusside reagent (prepared by mixing equal amounts of 10% sodium hydroxide, 10% sodium nitroprusside and 10% potassium ferricyanide solution and diluting the mixture to threefold with water) to a sample containing N-methyl-hydantoin. The mixture is allowed to stand at room temperature for a certain period of time, generally for 15 to 30 minutes, for color formation; and the amount of N-methyl-hydantoin is then calculated by measuring the optical density at 500 mμ.

The determination of the amount of ammonia formed by the reaction can be carried out according to any of the known physicochemical or enzymatic methods. Suitable physicochemical methods include the titration method, Nessler's test method, ninhydrin test method, Berthelot's reaction method and phenosafranine reaction method.

By the titration method, the amount of ammonia in the sample is determined by neutralization titration of the sample solution with a standard solution of an acid or by back titration of the sample in which the formed ammonia is absorbed by a certain amount of acid (Biochem. Z. 152, 1, 1924).

According to Nessler's test method, the sample containing ammonia is treated with Nessler reagent to form color and the amount of ammonia is colorimetrically determined (Standard Methods of Clinical Chemistry Vol. 2, p. 186, Academic Press, N.Y., 1958).

The ninhydrin test method is a method according to which the formed ammonia is reacted with ninhydrin and the amount of the reaction product is colorimetrically determined (J. Lab. Clin. Med., 49, 779, 1957).

According to Berthelot's reaction method, the ammonia in the sample is reacted with phenol reagent and alkaline sodium hypochlorite reagent to form color and the amount of ammonia in the sample is colorimetrically determined (Clin. Chimica, Acta, 8, 5, 1963).

The phenosafranine reaction method utilizes the phenomenon that phenosafranine (red-colored) is decolorized in proportion to the amount of hypochlorite. According to this method, the sample containing ammonia is reacted with hypochlorite; to the mixture is then added a safranine solution for decolorization in proportion to the concentration of the residual hypochlorite; and the amount of ammonia is calculated after the absorbency of the solution of the residual safranine is measured (Proc. Soc. Exptl. Biol. Med., 93, 589, 1956).

A suitable enzymatic method for the determination of the amount of ammonia utilizes L-glutamate dehydrogenase (EC 1.4.1.2, hereinafter referred to as GLDH) which is an NAD (nicotinamide-adenine dinucleotide) oxido-reductase. GLDH is an enzyme which catalyzes the reaction to form L-glutamic acid from 2-oxoglutarate and ammonia. In the absorption spectrum of NAD which acts as a co-enzyme in this reaction, NAD either of the oxidized type or of the reduced type shows a maximum absorption at 260 mμ. The reduced type NAD shows another maximum absorption at 340 mμ but the oxidized type NAD does not. Therefore, the absorbency at 340 mμ can be utilized for the quantitative determination of the reduced type NAD ($NADH_2$). Applying this measurement, the amount of ammonia can be determined by carrying out an enzymatic reaction of ammonia in the sample with 2-oxoglutarate using GLDH as the enzyme and NAD as a co-enzyme and measuring the decrease in the absorbency of the reaction mixture at 340 mμ.

The amount of creatinine in human blood serum is measured according to the method of the present invention and also the conventional method. The results are shown in the following Table I.

In Table I, the conventional method is based on the method described in Kitamura, Genshi; Jissen Rinsho Kagaku (Practice of Therapeutic Chemistry), Ishiyaku Shuppan Kabushiki Kaisha, p. 243–255, 1974.

Also in Table I, for the determination of the formed ammonia, the method of the present invention employs, as a typical physicochemical method, the modified method of the method of Okuda and Fujii (Saishin Igaku, 21, 622, 1966) using Berthelot's reaction and, as the enzymatic method using GLDH, the method of A. Levitzki (Anal. Biochem. 33, 335, 1970). For the determination of the amount of N-methyl-hydantoin formed using the method of the present invention, the method of Kirby and Berry (Paper and Paperelectrophoresis, page 348) is employed.

threefold. The precipitate is then dissolved in 500 ml of 0.01M phosphate buffer (pH 7.0) and the solution is dialyzed for 48 hours in a dialyzer of cellophane tube against 20 l of 0.01M phosphate buffer (pH 7.0) while changing the solvent every 12 hours. Thereafter, in order to remove nucleic acid, 100 ml of 3% aqueous solution of protamine (product of Nakarai Kagaku Yakuhin Kabushiki Kaisha) is added gradually to 1 l of dialyzate with stirring and the resultant mixture is allowed to stand at 0°–4° C. for about 30 minutes to form a precipitate. The thus formed precipitate is removed by centrifugation (10,000 × g, 20 minutes). The yield in terms of activity of creatinine desimidase contained in Table I

| | | Comparative Determination of the Amount of Creatinine | | | |
|---|---|---|---|---|---|
| | | **Mean value of the determined amount of creatinine in the same serum | Simultaneous reproducivility | | |
| | Method | | Standard deviation | Coefficient of variation | Name of the used kit |
| Conventional method | Method described in Jissen Rinsho Kagaku, p. 243-255, 1974 | 4.82 | 0.13 | 2.66 | Kyokuto Creatinine reagent (Product of Kyokuto Shiyaku Kabushiki Kaisha) |
| | | 4.65 | 0.16 | 3.83 | Creatinine test Wako (Product of Wako Junyaku Kabushiki Kaisha) |
| Method of the present invention | Method measuring the amount of formed ammonia | Modified method of the method of Okuda and Fujii | 3.60 | 0.11 | 1.20 | Ammonia test Wako (Product of Wako Junyaku Kabushiki Kaisha) |
| | | Method using the enzyme GLDH | 3.71 | 0.10 | 1.05 | The enzyme GLDH is a product of Oriental Chemicals Co. |
| | Method measuring the amount of formed N-methyl-hydantoin | | 3.43 | 0.28 | 3.60 | *Reagent preparation |

*reagent preparation
prepared by mixing equal amounts of 10% sodium hydroxide, 10% sodium nitroprusside and 10% potassium ferricyanide and diluting the mixture to threefold with water
**mean value when the amount of creatinine in serum is determined for 20 times.

From the results illustrated in the foregoing Table I, those skilled in the art will readily appreciate that the method for creatinine determination according to the present invention provides superior results with enhanced simultaneous reproducibility.

Certain specific embodiments of the invention are illustrated by the following representative examples.

EXAMPLE 1

In this example, a culture of *Brevibacterium ammoniagenes* KY 3462, FERM-P No. 3207, ATCC 31169 is inoculated into 10 l of a culture medium comprising 2 g/dl glucose, 0.5 g/dl creatinine hydrochloride, 0.1 g/dl $K_2HPO_4$, 0.05 g/dl $MgSO_4.7H_2O$, 0.05 gl/dl KCl and 0.1 g/dl yeast extract (pH 7.5) in a 30 l-jar fermenter and cultured with aeration and stirring at 30° C. for 24 hours. Then, 10 l of the culture liquor is treated in a continuous centrifuge and about 100 g of microbial cells are collected. The cells are washed with 5 l of 0.01M phosphate buffer (pH 7.0) and suspended in 2 l of 0.01M phosphate buffer (pH 7.0). The suspension is subjected to treatment using DYNOMILL (product of Willy A. Bachofen, Switzerland) to grind the cells. After grinding, the product is subjected to centrifugation (20,000 × g, 20 minutes) using a refrigerated centrifuge and the supernatant is recovered. About 30 g of a precipitate is obtained by treating the supernatant with ammonium sulfate of 40–70% saturation. The yield in terms of activity of creatinine desimidase contained in the precipitate is 80% and the specific activity is elevated to the supernatant is 90% and the specific activity is elevated to twofold. The supernatant is passed through a column of 1 kg of DEAE-cellulose (product of Pharmacia Fine Chemicals, Sweden) previously treated with 0.01M phosphate buffer (pH 7.0) to effect adsorption of the creatinine desimidase. The column is then washed with 0.01M phosphate buffer (pH 7.0) to remove impure proteins. Thereafter, a concentration gradient of from 0.01M phosphate buffer (pH 7.0) to 0.1M phosphate buffer (pH 7.0) containing 0.3M NaCl is prepared and passed through the column. The active fractions of creatinine desimidase are eluted forming a single peak. The active fractions are combined and two volumes of acetone is added thereto to obtain a precipitate. The precipitate is collected by centrifugation (10,000 × g, 20 minutes) and dissolved in 100 ml of water which has been demineralized through ion exchange treatment. The solution is dialyzed in a dialyzer of cellophane tube against 0.01M phosphate buffer (pH 7.0) and the dialyzate is freeze-dried whereby about 1 g of purified creatinine desimidase exhibiting a specific activity of 2.5 units/mg is obtained. The total yield in terms of activity of creatinine desimidase is 56% and the specific activity is about 60-fold.

EXAMPLE 2

In this example, *Corynebacterium lilium* KY 3509, FERM-P No. 3209, ATCC 15990 is used as the culture strain and a medium comprising 3 ml/dl bonito meat extract (containing about 3.3 g/dl creatinine), 0.5 g/dl peptone and 0.5 g/dl glucose (pH 7.5) is used. Culturing is carried out in the same manner as described in Example 1. As a result, about 150 g of the microbial cells are obtained. The cells are subjected to the extraction and purification procedure as described in Example 1 to obtain about 1.5 g of purified creatinine desimidase exhibiting a specific activity of 1.5 units/mg. The yield is 55%.

EXAMPLE 3

In this example, *Pseudomonas ovalis* KY 4651, FERM-P No. 3211, ATCC 31171 is cultured in a medium comprising 3 g/dl beef extract, 0.5 g/dl peptone and 0.3 g/dl glucose (pH 7.5). Culturing is carried out in the same manner as described in Example 1, to obtain about 180 g of microbial cells. The cells are subjected to the extraction and purification procedure as described in Example 1 to obtain about 2 g of purified creatinine desimidase exhibiting a specific activity of 1.0 unit/mg. The yield is 57%.

EXAMPLE 4

In this example, *Arthrobacter ureafaciens* KY 3152, FERM-P No. 3213, ATCC 7562 is cultured in the same manner as described in Example 1. As a result, about 150 g of the microbial cells are obtained. The cells are subjected to the extraction and purification procedure as described in Example 1 to obtain about 0.5 g of purified creatinine desimidase exhibiting a specific activity of 2.0 units/mg. The yield is 57%.

EXAMPLE 5

In this example, 10 l of a culture liquor obtained by carrying out culturing in the same manner as described in Example 1 is subjected to continuous centrifugation to obtain 9.5 l of a supernatant. The supernatant is treated with ammonium sulfate of 40-70% saturation to obtain about 5 g of a precipitate. The yield in terms of activity of creatinine desimidase contained in the precipitate is 80% and the specific activity is elevated to threefold. The precipitate is dissolved in 100 ml of 0.01M phosphate buffer (pH 7.0) and the solution is dialyzed for 48 hours in a dialyzer of cellophane tube against 20 l of 0.01M phosphate buffer (pH 7.0) while changing the solvent every 12 hours. Then, 200 ml of the dialyzate is subjected to removal of nucleic acid, DEAE-cellulose column chromatography, precipitation with acetone and freeze-drying in the same manner as described in Example 1. About 120 mg of purified creatinine desimidase exhibiting a specific activity of 2.0 units/mg is obtained. The yield is 52%.

EXAMPLE 6

In this example, cultures of the strains identified in the following Table II are inoculated into 50 ml of a medium having the same composition as in Example 1 in 500 ml-Sakaguchi flasks, respectively and are cultured at 30° C. for 24 hours with shaking. The culture liquors are treated with a refrigerated centrifuge (10,000 × g, 20 minutes) and the microbial cells are collected. Then, 0.5 g of the cells are washed with 50 ml of 0.01M phosphate buffer (pH 7.0) and suspended in 10 ml of 0.01M phosphate buffer (pH 7.0). The suspensions are subjected to ultrasonic treatment for 20 minutes using an ultrasonic disintegrator (product of Kaijo Denki Kabushiki Kaisha) and further to refrigerated centrifugation (20,000 × g, 20 minutes). The thus obtained supernatants are recovered and the creatinine desimidase activity and protein concentrations are measured. The results are shown in the following Table II.

Table II

| Strains | Creatinine desimidase activity | |
|---|---|---|
| | unit/mg-protein | unit/mg-cultured mass* |
| *Brevibacterium ammoniagenes* KY 3462 | 0.042 | 0.185 |
| *Brevibacterium divaricatum* KY 3810 | 0.012 | 0.093 |
| *Corynebacterium lilium* KY 3509 | 0.040 | 0.175 |
| *Corynebacterium glutamicum* KY 3801 | 0.010 | 0.073 |
| *Pseudomonas ovalis* KY 4651 | 0.016 | 0.112 |
| *Pseudomonas cruciviae* KY 3961 | 0.011 | 0.062 |
| *Arthrobacter ureafaciens* KY 3152 | 0.025 | 0.120 |
| *Arthrobacter histidinolovorans* KY 3158 | 0.020 | 0.060 |

*in terms of activity/ml of cultured mass (culture liquor and the cells).

EXAMPLE 7

In this example, 20 μl of serum (product of American Hospital Supply Corporation, Dade Division, U.S.A., sold under the trade name of Moni-trol I, containing 1.1 mg/dl of creatinine) and 20 μl of a standard solution of creatinine (an aqueous solution containing 400 μg/dl of creatinine) are respectively added to a solution consisting of 1.0 ml of an enzyme solution (0.01M phosphate buffer of pH 7.5 containing 0.1 mg of creatinine desimidase having a specific activity of 0.1 unit/mg) and 1.0 ml of 0.1M phosphate buffer (pH 7.5) and the resulting mixtures are incubated respectively at 37° C. for 10 minutes.

After the reaction period, 1 ml of phenol reagent (prepared by dissolving 5.0 g of phenol and 25 mg of sodium nitroprusside in water to make a total volume of 500 ml) and 1 ml of alkaline sodium hypochlorite reagent (prepared by dissolving 2.5 g of sodium hydroxide in about 300 ml of water, adding 1.25 ml of sodium hypochlorite to the solution and supplementing the mixture with water to make a volume of 500 ml) are added to the mixtures which are then allowed to stand at 37° C. for 20 minutes to form color and are used as the test solutions.

Separately, 20 μl of serum and 20 μl of the standard solution of creatinine are added respectively to a solution consisting of 1.0 ml of the enzyme solution and 1.0 ml of 0.1M phosphate buffer (pH 7.5). At the same time, 1 ml of phenol reagent and 1 ml of alkaline sodium hypochlorite reagent are added thereto and the resulting mixtures are used as blank solutions.

The optical density of the test solutions are measured at 640 mμ against the blank solutions. From the measurement of the standard solution of creatinine, the calibration curve of the optical density at 640 mμ and the concentration of creatinine is obtained. Based on this data, the concentration of creatinine in the serum is calculated from the measurement of the optical density of the serum at 640 mμ.

The results are shown in the following Tables III and IV. Table III shows the values when the amount of creatinine in the standard serum is determined successively for 10 times and the standard deviation and coefficient of variation are calculated from these values.

Table IV shows the results when the amount of creatinine in 20 samples of serum is determined by the method of the present invention and known method.

Table III

| Test No. | Amount of creatinine determined (mg/dl) |
|---|---|
| 1 | 1.00 |
| 2 | 1.07 |
| 3 | 1.01 |
| 4 | 1.09 |
| 5 | 1.00 |
| 6 | 0.98 |
| 7 | 1.02 |
| 8 | 1.00 |
| 9 | 1.05 |
| 10 | 1.02 |
| Mean value | 1.02 |
| Standard deviation | 0.03 |
| Coefficient of variation | 2.94 |

Table IV

| Sample | Amount of creatinine determined (mg/dl) | |
|---|---|---|
|  | Method of the present invention | Method of Jaffe |
|  | (Yi) | (Xi) |
| Serum 1 | 1.09 | 1.50 |
| 2 | 0.85 | 1.30 |
| 3 | 1.21 | 1.76 |
| 4 | 0.51 | 0.73 |
| 5 | 1.52 | 1.91 |
| 6 | 0.59 | 0.93 |
| 7 | 1.10 | 1.43 |
| 8 | 1.17 | 1.63 |
| 9 | 1.09 | 1.42 |
| 10 | 0.85 | 1.12 |
| 11 | 1.03 | 1.25 |
| 12 | 0.41 | 0.63 |
| 13 | 0.66 | 0.92 |
| 14 | 0.51 | 0.71 |
| 15 | 0.21 | 0.33 |
| 16 | 0.57 | 0.88 |
| 17 | 0.58 | 0.79 |
| 18 | 1.60 | 2.01 |
| 19 | 1.55 | 2.03 |
| 20 | 1.46 | 1.85 |
| Mean value | $\overline{Y} = 0.93$ | $\overline{X} = 1.26$ |

Coefficient of correlation $\gamma = \dfrac{\epsilon(Xi - \overline{X})(Yi - \overline{Y})}{\sqrt{\epsilon(Xi - \overline{X})^2 \epsilon(Yi - \overline{Y})^2}} = 0.99$ Regression $Y = 0.81 X - 0.09$

EXAMPLE 8

In this example, 20 μl of serum (Moni-trol I) and 20 μl of a standard solution of creatinine (an aqueous solution containing 400 μg/dl of creatinine) are respectively added to 1.0 ml of a creatinine desimidase solution (0.01M phosphate buffer of pH 7.5 containing 0.1 mg of creatinine desimidase having a specific activity of 0.1 unit/mg) and 1.0 ml of 0.1M phosphate buffer (pH 7.5) and the resulting mixtures are incubated respectively at 37° C. for 10 minutes.

To the reaction mixtures are added 1 ml of 4 mM NADH (product of Merck & Co.), 40 mM 2-oxoglutarate and 1 ml of a solution of L-glutamate dehydrogenase [containing 0.1 mg of L-glutamate dehydrogenase (product of Oriental Yeast Kabushiki Kaisha) having a specific activity of 90 units/mg or more], respectively, and the resulting mixtures are incubated at 37° C. for 10 minutes. The decrease in absorption of the reaction mixtures at 340 mμ is measured.

The results are shown in Tables V and VI.

Table V shows the values when the amount of creatinine in the standard serum is determined successively for 10 times and the standard deviation and coefficient of variation are calculated from the obtained values.

Table VI shows the results when the amount of creatinine in 20 samples of serum is determined by the method of the present invention and known method.

Table V

| Test No. | Amount of creatinine determined (mg/dl) |
|---|---|
| 1 | 1.07 |
| 2 | 1.04 |
| 3 | 1.15 |
| 4 | 1.05 |
| 5 | 1.08 |
| 6 | 1.11 |
| 7 | 1.16 |
| 8 | 1.09 |
| 9 | 1.12 |
| 10 | 1.03 |
| Mean value | 1.09 |
| Standard deviation | 0.04 |
| Coefficient of variation | 3.67 |

Table VI

| Sample | Amount of creatinine determined (mg/dl) | |
|---|---|---|
|  | Method of the present invention | Method of Jaffe |
|  | (Yi) | (Xi) |
| Serum 1 | 1.12 | 1.50 |
| 2 | 0.89 | 1.30 |
| 3 | 1.32 | 1.76 |
| 4 | 0.59 | 0.73 |
| 5 | 1.55 | 1.91 |
| 6 | 0.62 | 0.93 |
| 7 | 1.15 | 1.43 |
| 8 | 1.21 | 1.63 |
| 9 | 1.13 | 1.42 |
| 10 | 0.88 | 1.12 |
| 11 | 1.18 | 1.25 |
| 12 | 0.43 | 0.63 |
| 13 | 0.63 | 0.92 |
| 14 | 0.53 | 0.71 |
| 15 | 0.22 | 0.33 |
| 16 | 0.61 | 0.88 |
| 17 | 0.60 | 0.79 |
| 18 | 1.62 | 2.01 |
| 19 | 1.60 | 2.03 |
| 20 | 1.48 | 1.85 |
| Mean value | $\overline{Y} = 0.97$ | $\overline{X} = 0.126$ |

Coefficient of correlation $\gamma = 0.99$
Regression $Y = 0.83 X - 0.08$

EXAMPLE 9

In this example, 20 μl of serum (Moni-trol I) and 20 μl of a standard solution of creatinine (an aqueous solution containing 400 μg/dl of creatinine) are respectively added to a solution consisting of 1.0 ml of an enzyme solution (0.01M phosphate buffer of pH 7.5 containing 0.1 mg of creatinine desimidase having a specific activity of 0.1 unit/mg) and 1.0 ml of 0.1M phosphate buffer (pH 7.5) and the resulting mixtures are incubated respectively at 37° C. for 10 minutes.

To the reaction mixtures is then added 1 ml of alkaline ferricyanide-nitroprusside reagent (prepared by mixing equal amounts of 10% sodium hydroxide, 10% sodium nitroprusside and 10% potassium ferricyanide solution and diluting the mixture to threefold with water) and the resulting mixtures are allowed to stand at room temperature for 20 minutes to form color and are used as the test solutions.

Separately, 20 μl of serum and 20 μl of the standard solution of creatinine are added, respectively, to a solution consisting of 1.0 ml of the enzyme solution and 1.0 ml of 0.1M phosphate buffers (pH 7.5), to which is added, at the same time, 1 ml of alkaline ferricyanide-nitroprusside reagent. The resulting mixtures are used as blank solutions.

The optical density of the test solutions are measured at 500 mµ against the blank solutions. From the measurement of the standard solution of creatinine, the calibration curve of the optical density at 500 mµ and the concentration of creatinine is obtained. Based on this, the concentration of creatinine in the serum is calculated from the measurement of the optical density of the serum at 500 mµ.

The results are shown in Tables VII and VIII.

Table VII shows the values when the amount of creatinine in the standard serum is determined successively for 10 times and the standard deviation and coefficient of variation are calculated from the obtained values.

Table VIII shows the results when the amount of creatinine in 20 samples of serum is determined by the method of the present invention and known method.

Table VII

| Test No. | Amount of creatinine determined (mg/dl) |
|---|---|
| 1 | 1.10 |
| 2 | 1.09 |
| 3 | 1.16 |
| 4 | 1.13 |
| 5 | 1.17 |
| 6 | 1.15 |
| 7 | 1.09 |
| 8 | 1.11 |
| 9 | 1.13 |
| 10 | 1.12 |
| Mean value | 1.12 |
| Standard deviation | 0.02 |
| Coefficient of variation | 1.78 |

Table VIII

| Sample | Amount of creatinine determined (mg/dl) | |
|---|---|---|
| | Method of the present invention | Method of Jaffe |
| | (Yi) | (Xi) |
| Serum 1 | 1.20 | 1.50 |
| 2 | 1.00 | 1.30 |
| 3 | 1.39 | 1.76 |
| 4 | 0.61 | 0.73 |
| 5 | 1.62 | 1.91 |
| 6 | 0.65 | 0.93 |
| 7 | 1.21 | 1.43 |
| 8 | 1.31 | 1.63 |
| 9 | 1.18 | 1.42 |

Table VIII-continued

| Sample | Amount of creatinine determined (mg/dl) | |
|---|---|---|
| | Method of the present invention | Method of Jaffe |
| 10 | 0.90 | 1.12 |
| 11 | 1.00 | 1.25 |
| 12 | 0.48 | 0.63 |
| 13 | 0.71 | 0.92 |
| 14 | 0.57 | 0.71 |
| 15 | 0.27 | 0.33 |
| 16 | 0.59 | 0.88 |
| 17 | 0.63 | 0.79 |
| 18 | 1.68 | 2.01 |
| 19 | 1.62 | 2.03 |
| 20 | 1.51 | 1.85 |
| Mean value | $\overline{Y} = 1.07$ | $\overline{X} = 1.26$ |

Coefficient of correlation $\gamma = 0.99$
Regression $Y = 0.84 X - 0.05$

What is claimed is:

1. A method for the quantitative determination of creatinine in a sample which comprises reacting said sample with a solution of creatinine desimidase until said creatinine is hydrolyzed to form ammonia and N-methyl-hydantoin and then measuring the amount of at least one of said ammonia and N-methyl-hydantoin formed by said reaction.

2. A method according to claim 1 wherein said reaction is carried out at about 30°–50° C. for about 10–30 minutes.

3. A method according to claim 1 wherein said sample is urine.

4. A method according to claim 1 wherein said sample is blood serum.

5. A method according to claim 1 wherein said creatinine desimidase is derived from a microorganism belonging to the genus *Brevibacterium, Corynebacterium, Pseudomonas* or *Arthrobacter*.

6. A method according to claim 5 wherein said microorganism is selected from the group consisting of *Brevibacterium ammoniagenes, Brevibacterium divaricatum, Corynebacterium lilium, Corynebacterium glutamicum, Pseudomonas ovalis, Pseudomonas cruciviae, Arthrobacter ureafaciens* and *Arthrobacter histidinolovorans*.

7. A method according to claim 6 wherein said microorganism is selected from the group consisting of *Brevibacterium ammoniagenes* ATCC 31169, *Brevibacterium divaricatum* ATCC 14020, *Corynebacterium lilium* ATCC 15990, *Corynebacterium glutamicum* ATCC 31170, *Pseudomonas ovalis* ATCC 31171, *Pseudomonas cruciviae* ATCC 31172, *Arthrobacter ureafaciens* ATCC 7562 *Arthrobacter histidinolovorans* ATCC 11442.

* * * * *